US012758433B2

(12) United States Patent
Harrison

(10) Patent No.: US 12,758,433 B2
(45) Date of Patent: Oct. 13, 2026

(54) WEIGHTLIFTING WRIST WRAP

(71) Applicant: Power Gripps USA, Inc., Hancock, ME (US)

(72) Inventor: Glenn Harrison, Summit, NJ (US)

( * ) Notice: Subject to any disclaimer, the term of this patent is extended or adjusted under 35 U.S.C. 154(b) by 98 days.

(21) Appl. No.: 18/792,511

(22) Filed: Aug. 1, 2024

(65) Prior Publication Data

US 2026/0033994 A1 Feb. 5, 2026

(51) Int. Cl.
*A61F 13/10* (2006.01)
*A63B 21/072* (2006.01)

(52) U.S. Cl.
CPC .......... *A61F 13/108* (2013.01); *A63B 21/072* (2013.01)

(58) Field of Classification Search
CPC ............................ A61F 13/108; A63B 21/072
See application file for complete search history.

(56) References Cited

U.S. PATENT DOCUMENTS

| | | | | |
|---|---|---|---|---|
| 4,247,101 A | 1/1981 | Gallmeyer | | |
| 5,620,399 A * | 4/1997 | Hofmann | A63B 21/4035 | 482/44 |
| 5,704,883 A * | 1/1998 | Eckmann | A63B 21/065 | 482/139 |
| 6,102,880 A | 8/2000 | Nelson et al. | | |
| 6,146,319 A | 11/2000 | Tarail | | |
| 6,893,410 B1 * | 5/2005 | Hely | A61F 13/108 | 602/21 |
| 7,051,377 B1 * | 5/2006 | Milner | A63B 71/141 | 2/161.6 |
| 10,695,603 B1 | 6/2020 | Lamping | | |
| 2003/0154538 A1 * | 8/2003 | Murphy | A63B 21/4019 | 2/160 |
| 2005/0075227 A1 * | 4/2005 | Emick | A63B 21/4001 | 482/139 |
| 2005/0255973 A1 * | 11/2005 | Ward | A63B 21/4001 | 482/93 |
| 2008/0120755 A1 * | 5/2008 | Ingram | A63B 21/4001 | 2/20 |
| 2008/0125295 A1 * | 5/2008 | Ingram | A63B 21/4021 | 2/161.1 |
| 2019/0142083 A1 * | 5/2019 | Amrhein | A41D 27/10 | 2/84 |
| 2020/0306126 A1 * | 10/2020 | Carvalho | A41D 13/088 | |

OTHER PUBLICATIONS

"RDX W3 IPL USPA Approved Powerlifting Wrist Support Wraps with Thumb Loops OEKO-TEX Standard 100 certified," RDX Sports [online] Retrieved from the Internet <URL: https://rdxsports.com/products/w3-power-weightlifting-wrist-wraps> [retrieved on Oct. 29, 2024], (c) 2024, 12 pages.

* cited by examiner

*Primary Examiner* — Sundhara M Ganesan
(74) *Attorney, Agent, or Firm* — McLane Middleton, Professional Association

(57) ABSTRACT

A wrist wrap for use in supporting a wrist during weightlifting includes a strip, at least one tab, and first and second fastener sections. The tab extends from a first end of the strip and is made of a single ply of tab material. The first and second fastener sections are disposed on the wrist wrap so as to engage one another to secure one to the other. A user may hold the end of the tab in place with a tip of a finger, thereby holding the strap in place against her wrist while she uses the other hand to wrap and secure the strap. She may then tuck the tab into the wrappings.

24 Claims, 11 Drawing Sheets

12
32
18
30, 34

12
32
18
44

12
32
18
44

12
32
18
30, 34
20
48

12
32
18
44
46
20
48

12
32
18
44, 46
20
48

WEIGHTLIFTING WRIST WRAP

BACKGROUND

The present disclosure relates generally to weightlifting accessories, and specifically to an improved wrist wrap for use in weightlifting.

Wrist wraps are commonly used in weightlifting to prevent hyperextension of the wrist and promote proper wrist placement with respect to a bar. Wrist wraps allow for better weight stabilization without relying on non-targeted muscle groups for corrective movements. Optimum wrist wrap functionality depends on its proper placement around the wrist joint and slightly above and below. Without a second person, however, the process of putting on a prior art wrist wrap is necessarily a one-handed exercise, when two are needed for proper positioning of the wrap. Many wrist wraps are a simple strip of material with some means for attaching the material to itself. These means are often hook and loop-type fasteners. The user places one end of the wrap at her wrist and then needs to hold that end in place while also wrapping the remainder of the wrap around the wrist. Typically, the user will contort her hand to try to get a finger on the end of the wrist wrap to hold the wrap when the finger is on the same hand as the wrist that is being wrapped and then wrap the remainder of the wrist wrap with her other hand. The contortion of the hand to get that finger on the end of the wrap, if even possible, will put the wrist in the wrong position for wrapping, thereby frustrating the entire purpose. Alternatively, she may awkwardly try to hold the wrist wrap in place and wrap it with the same hand, likely resulting in a loose and/or poorly positioned wrap.

In response to this predicament, many wrist wraps include a thumb loop at an end of the wrap. The user loops the thumb loop around her thumb, thereby holding the end of the wrap in place so that she can then use her other hand to complete the wrapping process. While the thumb loop eliminates the need for the hand to contort to hold the end of the wrap in place, the thumb loop remains in place once the wrist wrap is wrapped and the lifter wishes to lift. The existence of the thumb loop between the user's hand will slightly decrease the user's grip on the bar. It will also create a slight increase in distance between the user's hand and the bar where the thumb loop is positioned. This is especially critical at the angle between the thumb and the first finger, which is a key area in gripping the bar. While this slight decrease in grip and slight increase in distance may seem negligible, wrist wraps are typically used to ensure good form when lifting very heavy weights. In such scenarios, secure grip of the bar is essential, not just for good form but also for safety. Moreover, if the body is making micro-adjustments to account for inconsistent grip across the palm due to the presence of the thumb loop, then the focus of the exercise may be compromised by the assistance of other muscle groups. Finally and importantly, it is uncomfortable for the user to have the loop being pushed into her palm during the actual lifting.

It might be thought that a solution to this conundrum would be for the user to slip the thumb loop off of her thumb once the wrap is in place. A thumb loop large enough to provide room for the thumb to slip back through would not hold the end of the wrist wrap in the correct position, however, thus thwarting the primary purpose of the thumb loop.

It is also notable that wraps with thumb loops cannot be used by those without thumbs. The small but vital community of weightlifters that have lost one or both thumbs therefore cannot easily apply wrist wraps without aid.

Therefore there is a need for a weight-lifting wrist wrap that overcomes these deficiencies in the prior art.

SUMMARY

In a first aspect, a wrist wrap for use in supporting a wrist during weight-lifting comprises a strip made of strip material, at least one tab made of tab material, and first and second fastener sections. The strip has first and second ends on opposing ends of the strip, a strip length extending between the first and second ends: first and second parallel edges extending along the strip length between the first and second ends, a strip width extending between the first and second parallel edges: and first and second opposing sides, a strip thickness extending between the first and second opposing sides. The tab extends from the first end of the strip and is made of a single ply of tab material. The first fastener section is disposed on the first side of the strip. The second fastener section is disposed on the wrist wrap so as to engage the first section such that the first and second sections may be fastened to one another.

In a more limited aspect, the first end is a perpendicular line between the first and second parallel edges.

In another more limited aspect, the first end is a straight line between the first and second parallel edges, forming non-right angles with the first and second parallel edges.

In another more limited aspect, the first end is a curved line between the first and second parallel edges.

In another more limited aspect, the at least one tab forms an angle between 85 and 95 degrees with the first parallel edge.

In another more limited aspect, the at least one tab forms an angle with the first parallel edge, preferably between 45 and 135 degrees, and more preferably between 65 and 115 degrees.

In another more limited aspect, the at least one tab is at least two tabs extending from an intersection of the first end and the first parallel edge of the strap. In a still more limited aspect the two tabs form two different angles with the first parallel edge.

In another more limited aspect, the at least one tab is at least two tabs, one of which extends from an intersection of the first end and the first parallel edge of the strap and one of which extends from a position on the first parallel edge of the strap that is at a distance from the first end.

In another more limited aspect, the tab material extends beyond the at least one tab such that the tab material has at least one area of overlap with the strip material and the tab material and strip material are affixed to one another at the at least one area of overlap. In a still more limited aspect, the tab material and the strip material are stitched or adhered or stitched and adhered to one another at the at least one area of overlap. In a still more limited aspect, the at least one area of overlap extends across the entire strip between the first and second parallel edges.

In another more limited aspect, the at least one tab is first and second tabs, with the first tab forming an angle between 85 and 95 degrees with the first parallel edge and the second tab forming an angle between 85 and 95 degrees with the second parallel edge.

In another more limited aspect, the tab material of each of the first and second tabs extends beyond the first and second tabs, respectively, such that the tab material has first and second areas of overlap with the strip material and the tab material and strip material are affixed to one another at the first and second areas of overlap. In a still more limited aspect, the tab material and the strip material are stitched or adhered or stitched and adhered to one another at the first and second areas of overlap. In a still more limited aspect, the first tab, the first area of overlap, the second area of overlap, and the second tab are comprised of a single piece of tab material extending across and beyond the first end of the strip.

In another more limited aspect, the strip material and the tab material are the same and the strip and the tab are integrated, i.e., cut from a single piece of the strip/tab material.

In another more limited aspect, the second fastener is disposed on the second side of the strip.

In another more limited aspect, the second fastener section extends from the second end of the strip.

In another more limited aspect, the second fastener section has a second fastener width parallel to and less than the strip width. The second fastener section is centered between the first and second parallel edges of the strip. In a still more limited aspect, the second fastener section extends from the second end of the strip and the second end of the strip angles inward toward the second fastener section.

In a more limited aspect, the first fastener section has a first fastener width parallel to and less than the strip width. The first fastener section is centered between the first and second parallel edges of the strip.

In another more limited aspect, the strip material is a stretchable material. In a still more limited aspect, the strip material is woven from latex rubber textured polyester yarn.

In another more limited aspect, the tab material is nylon. In a still more limited aspect, the edges of the nylon tab are sealed to prevent fraying.

In another more limited aspect, the first fastener section comprises either hook or loop fastener and the second fastener section comprises the other of hook or loop fastener.

In another more limited aspect, the strip width is between 2 and 4 inches, preferably between 2.5 and 3.5 inches.

In another more limited aspect, the strip length is between 12 and 24 inches, preferably between 15 and 18 inches.

In another more limited aspect, the at least one tab has a tab length between 0.75 and 3 inches, preferably between 1 and 2 inches.

In another more limited aspect, the at least one tab has a tab length. In a still more limited aspect, the tab length is between 1 and 2 inches.

In another more limited aspect, the at least one tab includes an area of increased width at its tip. In a still more limited aspect, the area of increased width is shaped as a crossbar.

In a second aspect, a method for putting the wrist wrap of the first aspect onto a working wrist includes the steps of placing the wrist wrap against the working wrist such that the at least one tab extends upward over the working palm: simultaneously maintaining the working wrist in a straight position while curling at least one finger of the working hand down such that a tip of the at least one finger holds a tip of the at least one tab in place against the working palm: wrapping the strap around the working wrist to a desired tension with the non-working hand: and securing the strap in place by engaging the first and second fastener sections with one another.

In a more limited aspect, the method also includes the step, to be performed after the securing step, of tucking the at least one tab down into the wrapping of the wrist wrap.

One advantage of the wrist wrap of the present invention is that it may be properly positioned and put onto a working hand using only the working hand and the non-working hand.

Another advantage of the wrist wrap of the present invention is that the tab may be tucked into the wrapping so that there is no material between the hand and the weightlifting bar that could compromise grip.

Another advantage of the wrist wrap of the present invention is that the tab is formed of only a single ply of material so that it is not bulky or difficult to tuck into the wrappings of the wrist wrap.

Further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings, which are not to scale, are only for purposes of illustrating preferred embodiments and are not to be construed as limiting the invention.

DETAILED DESCRIPTION OF THE PREFERRED EMBODIMENTS

Detailed embodiments of the present development are disclosed herein: however, it is to be understood that the disclosed embodiments are merely exemplary of the invention, which may be embodied in various forms. Therefore, specific structural and functional details disclosed herein are not to be interpreted as limiting but merely as a basis for the claims and as a representative basis for teaching one skilled in the art to variously employ the present inventive concept in virtually any appropriately detailed structure. Further, the terms and phrases used herein are not intended to be limiting but rather to provide an understandable description of the present development.

The terms "a" or "an," as used herein, are defined as one or more than one. The term "another," as used herein, is defined as at least a second or more. The terms "including" and/or "having" as used herein, are defined as comprising (i.e., open transition).

All numbers herein are assumed to be modified by the term "about," unless stated otherwise. The recitation of numerical ranges by endpoints includes all numbers subsumed within that range (e.g., 1 to 5 includes, inter alia, 1, 1.5, 2, 2.75, 3, 3.80, 4, and 5). Accordingly, unless indicated to the contrary, the numerical parameters set forth in the present specification and attached claims are approximations that can vary depending upon the desired properties sought to be obtained by the presently disclosed subject matter.

As used herein, the term "about," when referring to a value, can encompass variations of, in some embodiments ±20%, in some embodiments ±10%, in some embodiments ±5%, in some embodiments ±1%, in some embodiments ±0.5%, in some embodiments ±0.1%, and in some embodiments to ±0.01%, from the specified amount, as such variations are appropriate in the disclosed materials and methods.

As used herein, specifically in reference to the at least one tab of the wrist wrap of the present invention, a "single ply of tab material" means that the tab material is not formed in a loop so that one could put one's fingers through the loop. The single ply of tab material may be formed from a single sheet of material. The single ply of material may be formed from two or more sheets of material sewn, adhered, or otherwise affixed to one another, but in no instance is the single ply of material formed from two sheets of material formed in a loop through which one could put one's fingers.

Figure 1A:
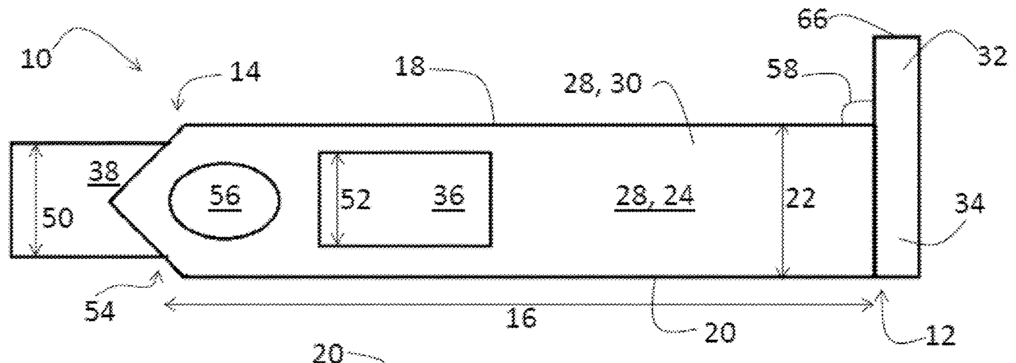
FIG. 1A is a top-down view of the first side of a wrist wrap according to the present invention.
Figure 1B:
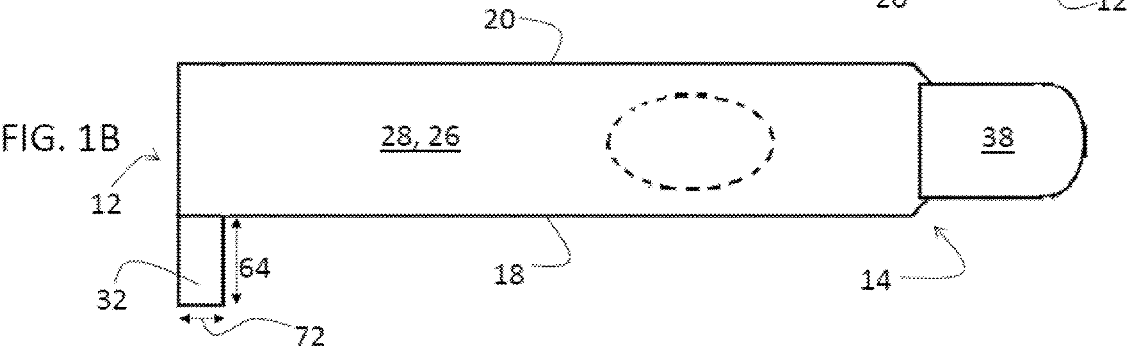
FIG. 1B is a top-down view of the second side of a wrist wrap according to the present invention.

Referring first to FIGS. 1A and 1B, top-down views of the first 24 and second 36 sides, respectively, of wrist wrap 10 of the present invention are provided. Wrist wrap 10 includes a strip 28 made of strip material 30, the strip 28 having first and second ends 12, 14 with a strip length 16 therebetween; first and second parallel edges 18, 20 with a strip width 22 therebetween; and first and second sides 24, 26 with a strip thickness 58 therebetween (shown. e.g., in FIGS. 2A-2D). First side 24 faces the viewer in FIG. 1A. Second side 26 faces the view in FIG. 1B. A tab 32 made of tab material 34 extends from first end 12 of strip 28 and includes tab tip 66, tab length 64, and tab width 72. A tab angle 58 is formed between the tab 32 and the first parallel edge 18 of the strip 28. As shown, tab angle 58 is substantially 90 degrees. (As used in this context, "substantially" indicates that the tab angle 58 is 90±5 degrees.) Wrist wrap 10 also includes first and second fastener sections 36, 38. In embodiments, first fastener section 36 has either hook or loop fastener and the second fastener section 38 has the other of hook or loop fastener so that first and second fastener sections 36, 38 will fasten to one another when engaged. A logo or other label 56 may be included anywhere on wrist wrap 10. The tab tip 66 is the opposite end of the tab 32 from 20) where the tab 32 intersects the first end 12 of the strip 28.

First fastener section 36 is disposed on the first side 24 of strip 28. Second fastener section 38 is disposed elsewhere on the wrist wrap 10 so that it is able to engage with first fastener section 36. In embodiments, such as that shown in FIG. 1A, second fastener section 38 extends from second end 14 of strip 28. In embodiments, the second end 14 angles inward 54 toward the second fastener section 38. In other embodiments, such as that shown in FIG. 4, second fastener section 38 is disposed on the second side 26 of strip 28. In embodiments, such as that shown in FIG. 2D, the first and second fastener sections 36, 38 are incorporated into and integrated with the strip material 30. In embodiments, such as that shown in FIG. 1A, first and/or second fastener sections 36, 38 are rectangular in shape. In embodiments, the first fastener section 36 has a first fastener width 52 parallel to and less than strip width 22, and first fastener section 36 is centered between the first and second parallel edges 18, 20. In embodiments, the second fastener section 38 has second fastener width 50 parallel to and less than strip width 22, and second fastener section 38 is centered between the first and second parallel edges 18, 20. As the hook and loop or other fastening means of the first and second fastener sections 36, 38 may be scratchy or otherwise irritating to the skin, having the first and second fastener widths 52, 50 less than the strip width 22 and centering the first and second fastener sections 36, 38 on the strip 28 may protect the user's skin from these irritants by ensuring they will not come in contact with the user's skin. In embodiments, such as that shown in FIG. 1B, first and/or second fastener section 36, 38 are rounded. In FIG. 1B, first fastener section 36 is not visible, but stitching, which is one way in which first fastener section 36 may be affixed to first side 24 of strip 28, indicates where the rounded first fastener section 36 is disposed on the first side 24. It is desirable for the first and second fastener sections 36, 38 to have sufficient area, particularly in the length dimension, to allow the wrist wrap 10 to be secured at a range of positions to account for the size of the user's wrist, the user's comfort, and the level of support desired by the user.

As will be described in more detail with reference to method 100, a user will place the wrist wrap 10 against her wrist such that the tab 32 is positioned over her palm. While keeping her wrist in the proper straight position to maximize effectiveness of the wrist wrap 10, she will curl one or more of her fingers down to hold the tip 66 of the tab 32 against her palm. The wrist wrap is then held in place while she wraps the strip 28 around her wrist with her other hand and affixes it in place with the first and second fastener sections 36, 38. The position of tab 32 at the first end 12 of the strip 28 is important so that all of the strip 28 is to one side of the tab 32 when it comes to wrapping, rather than a portion of the strip 28 extending on the other side as well. Once in place, the user tucks the tab 32 into the wrapped strip 28 of the wrist wrap 10. Unlike prior art wrist wraps that are a simple strip, she has been able to properly position and apply the wrist wrap without the assistance of another person. Unlike prior art wrist wraps with thumb loops, she does not have a bulky thumb loop between her hand and the bar compromising her grip and causing her discomfort. Notably, a lifter without a thumb would be able to properly position and apply this wrist wrap 10 without assistance from another person.

In embodiments, the strip material 30, out of which the strip 28 is made is a stretchable material. In embodiments, the strip material 30 is a latex rubber textured polyester yarn weave. In embodiments, the tab material 34, out of which the tab 32 is made is nylon. In embodiments, the tab material 34 is sealed to prevent fraying and other wear and tear on the tab 32. One of ordinary skill in the art will recognize that the strip material 30 and tab material 34 may be successfully made from many materials, however. In embodiments, such as those shown in FIGS. 2D, 5A, and 5D, the strip material 30 and the tab material 34 are the same. In other words, the strip 28 and the tab 32 are made from a single piece of material and are integrated one with the other. In embodiments, such as that shown in FIG. 1A, the tab material 34 extends across the first end 12 between first and second parallel edges 18, 20.

The tab 32 is formed from a single ply of tab material 34. Importantly, this single ply of tab material 34 is not formed in a loop so that one could put one's fingers through the loop. As the tab 32 will ultimately be tucked into the strip 28 wrapped around the wrist, it is important that it not be bulky, as it would be if it were formed into a loop, which would necessarily require at least two pieces of material. The tab material 34 is thin enough for easy tucking into the wraps of strip 28. In embodiments, the tab material 34 is nylon webbing, which is robust and easily tuckable into the wraps. The single ply of tab material 34 may be webbing or other woven sheets, but it is never formed into a loop.

In embodiments, strip length 16 is about 12 to 24 inches, preferably about 15 to 18 inches. In embodiments, strip width 22 is about 2 to 4 inches, more preferably about 2.5 to 3.5 inches, most preferably about 3 inches. In embodiments, the strip width 58 is about ⅛ inches. In embodiments, the tab 32 has a tab length 64 between about 0.75 and 3 inches, preferably between about 1 to 2 inches. The tab length 64 must be sufficient such that the tip of the user's finger can catch and hold the tip of the tab 32 against the working palm. Higher tab lengths 64 will only create more tab material 34 that needs to be tucked into the wrappings without providing additional functionality. The tab length 64 in the preferred range of 1 to 2 inches is sufficient for a tip of the user's finger(s) to meet the tab 32, and not so long that unnecessary additional tab material 34 is included in the tab 32. The tab length 64 is, therefore, not a design choice but a careful balance of factors between being long enough for the functionality of being able to be reached by the fingertip and not so long that the functionality of tucking the tab into the wrappings is compromised. These dimensions are merely exemplary. One of ordinary skill in the art will recognize that the wrist wrap 10 may be successfully developed in a broad range of each of its dimensions.

Figure 2A:
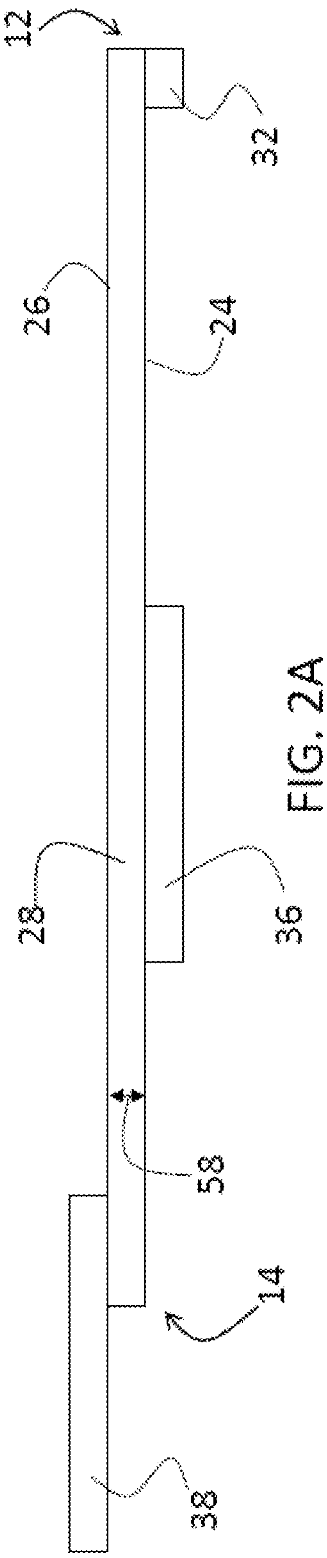
FIGS. 2A-2D are side views of various configurations of the wrist wrap according to the present invention.

Now referring to FIGS. 2A-2D, side views of wrist wrap 10 of the present invention are provided, illustrating variations on the disposition of first and second fastener sections 36, 38 and tab 32. The embodiment shown in FIG. 2A is similar to that shown in FIGS. 1A and 1B. First fastener section 36 is disposed on first side 24 of strip 28 and second fastener 30) section 38 extends from second end 14 of strip 28. The second fastener section 38 partially overlaps with and is affixed to the second side 26 of the strip 28. Tab 32 extends from first end 12 of strip 28 and tab material 34 overlaps with the first side 24 of strip 28. In the embodiment shown in FIG. 2B, tab material 34 overlaps with the second side 26 of strip 28. Whether to have the overlap (if an overlap is present) on the first side 24 or second side 26 may be a consideration regarding comfort for the user or ease of manufacture. In this embodiment, second fastener section 38 partially overlaps with and is affixed to the first side 24 of the strip 28. First and second fastener sections 36, 38 include hook and loop fastener, with the hook or loop of the first fastener section 36 always facing out from first side 24 and the other of the hook or loop of the second fastener section 38 always facing in the opposite direction. In both of FIGS. 2A and 2B, therefore, the working surface of the first fastener section 36, or the surface that has the hook or loop, is facing down or out from the first side 24. Similarly, the working surface of the second fastener section 38, or the surface that has the other of the hook or loop, is facing up or out from the second side 28 (in FIG. 2A). The working surface of the second fastener section 38 has a larger surface area in the embodiment shown in FIG. 2A as compared to FIG. 2B, which may be advantageous to ensure engagement by overlap of the first and second fastener sections 36, 38. Other considerations, such as ease of manufacture, for example, may be a consideration toward an embodiment according to FIG. 2B, however.

Figure 2B:
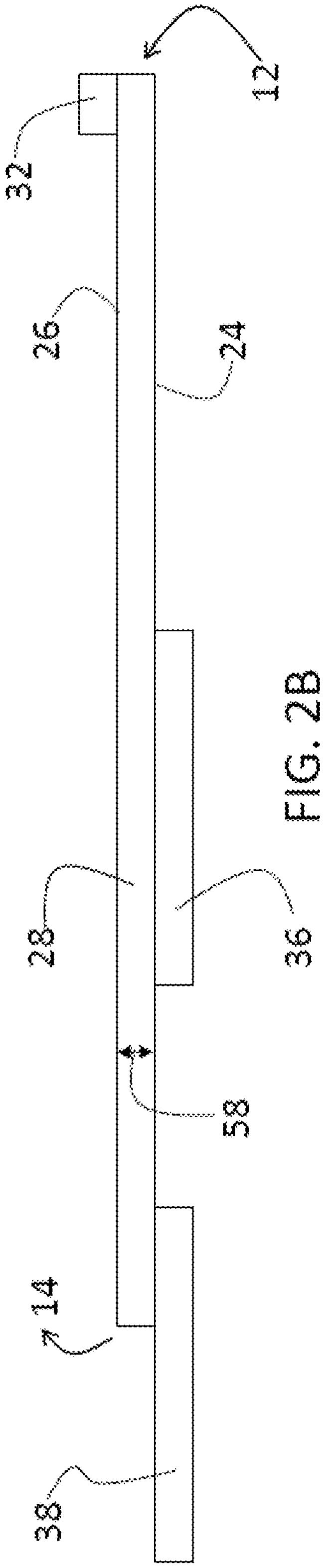
Figures 2C, 2D:
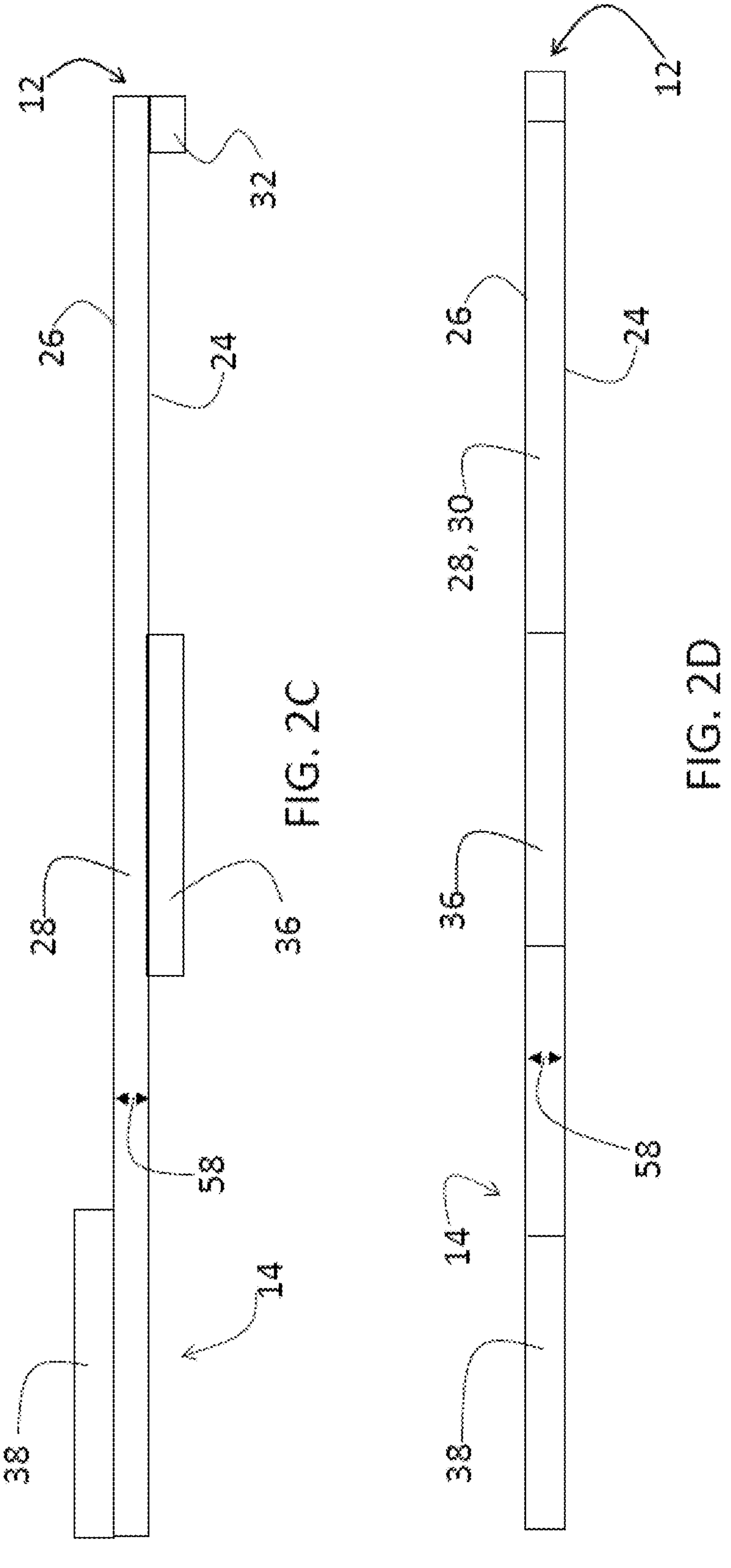

In the embodiment shown in FIG. 2C, second fastener section 38 completely overlaps second end 14 of strip 28, rather than extending therefrom, as shown in FIGS. 2A and 2B. In the embodiment shown in FIG. 2D, all sections are integrated. That is to say, strip material 30 and tab material 34 are the same and the strip 28 and tab 32 are formed of the same piece of material (as in the embodiments shown in FIGS. 5A and 5D). The hook and loop of first and second fasteners 36, 38 is also incorporated into the strip material 30, again with the hook or loop of first fastener section 36 facing down or out of first side 24 and the hook or loop of second fastener section 38 facing up or out of second side 26. In an embodiment such as that shown in FIG. 2D, there is no need for attachment or affixation of tab 32 or first or second fastener sections 36, 38 because the entire wrist wrap 10 is a single integrated piece.

Figure 3B:
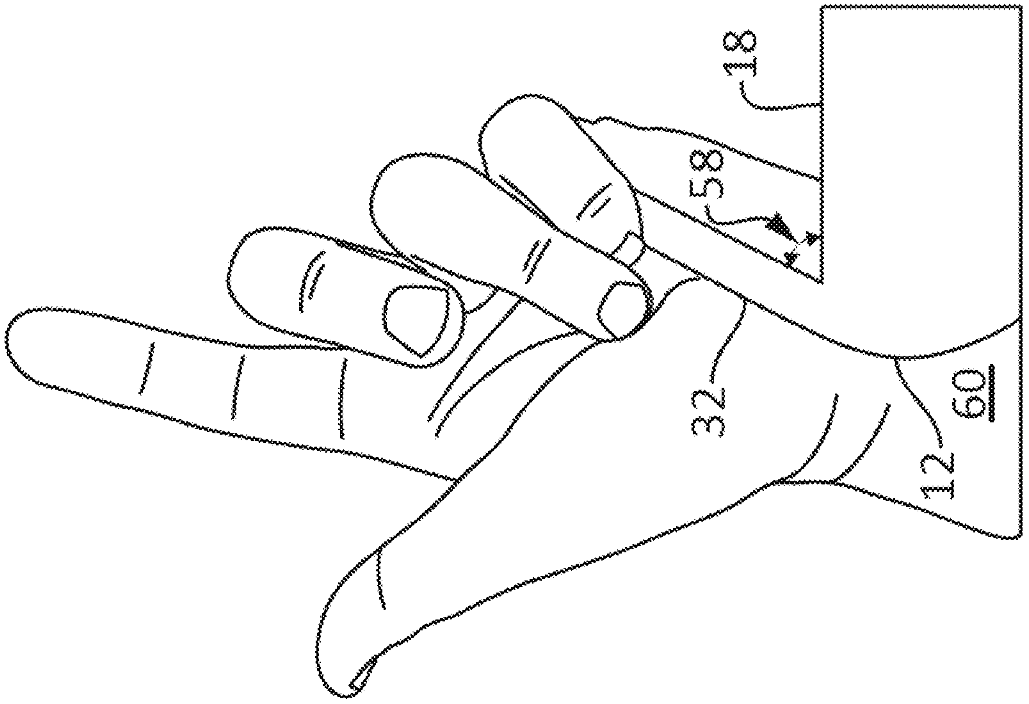
FIGS. 3A and 3B are illustrations of alternate configurations of the first end of the wrist wrap of the present invention superimposed over a human hand.
Figure 3A:
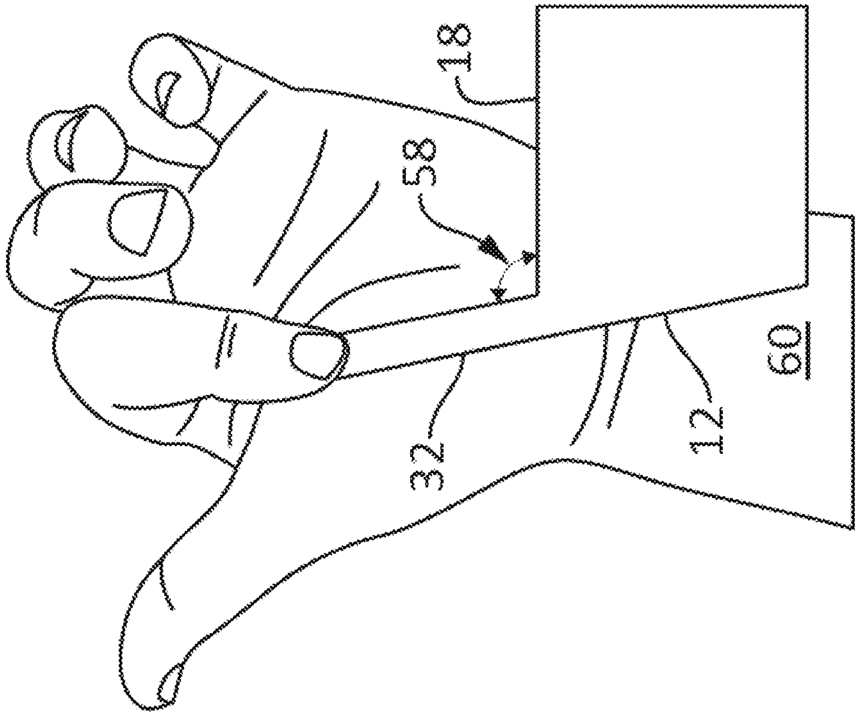
Figure 3C:
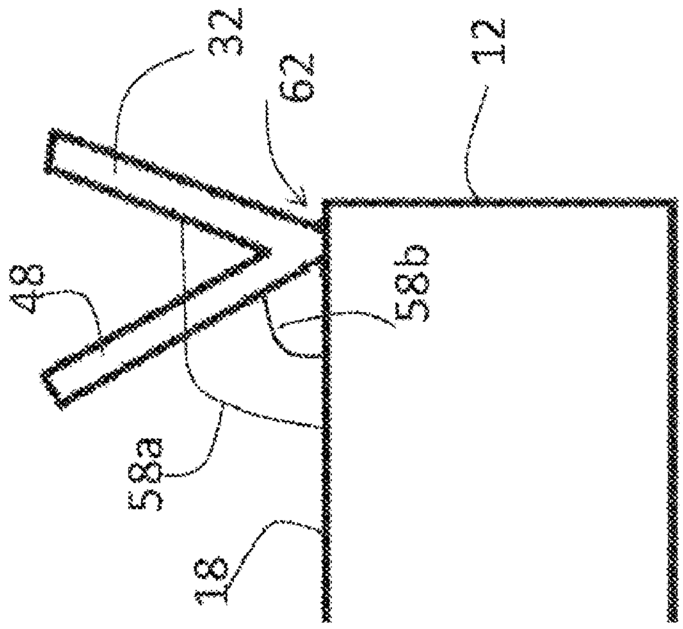
FIGS. 3C and 3D are top-down views of the first end of the strap with two tabs.

Now referring to FIGS. 3A-3C, illustrations of variations of the first end 12 and tab angle 58 are provided. As will be described in more detail below with reference to method 100 of the present invention, the wrist wrap 10 is designed for a weightlifter to be able to put the wrist wrap 10 on her working wrist 60 by holding the tab 32 with the tip of one or more of her fingers to hold the first end 12 of the wrist wrap 10 in place while the non-working hand wraps the remainder of the strip 28 and second end 14 of the wrist wrap 10 around the working wrist 60. In the embodiments shown in FIGS. 1A and 1B, for example, the tab 32 extends substantially perpendicularly out from the first parallel edge 18 of the strip 28. FIGS. 3A and 3B illustrate that the tab angle 58 may be greater or less than 90 degrees. In FIG. 3A, tab angle 58 is about 105 degrees, which facilitates using the tip of the pointer finger to hold tab 32 in place. In FIG. 3B, tab angle 58 is about 65 degrees, which facilitates using the tip of the pinky finger to hold tab 32 in place. It will be recognized that the tab angle 58 may be successful through a range, but preferably between about 45 and 135 degrees and more preferably between about 65 and 115 degrees. Different users may prefer to use the tips of different fingers to hold the tab 32 in place and different tab angles 58 will facilitate such preferences.

FIGS. 3A and 3B also illustrate variations on first end 12. In the embodiments shown in FIGS. 1A and 1B, for example, first end 12 is a straight line between first and second parallel edges 18, 20, creating about 90 degree angles with each. In embodiments such as that shown in FIG. 3A, however, first end 12 is a straight line between first and second parallel edges 18, 20, but angled so that the angles created between first end 12 and first and second parallel edges 18, 20 are greater or less than 90 degrees. In embodiments such as that shown in FIG. 3B, first end 12 is curved or has some other shape other than a straight line. As first end 12 will be held tightly against the working wrist 60, different shapes may increase comfort for the user by minimizing points and/or mitigating chafing.

In the embodiment shown in FIG. 3C, first and second tabs 32, 48 extend from an intersection 62 between the first end 12 and the first parallel edge 18 of the strip 28. Tab 32 forms a first tab angle **58*a* with first parallel edge 18 and tab 48 forms a second tab angle 58*b* with first parallel edge 18. Having two tabs 32, 48 with different angles 58*a*, 58*b* gives the user options as to which finger to use to hold the tab in place or to hold both tabs in place with two different fingers. Although neither tab angle 58*a* or 58*b* is a right angle, it is understood that in some embodiments one of tab angle 58*a* or 58*b* is about 90 degrees. In some embodiments, more than one tab 32 is included, each forming the same tab angle 58 with the first parallel edge 18**.

Figure 3D:
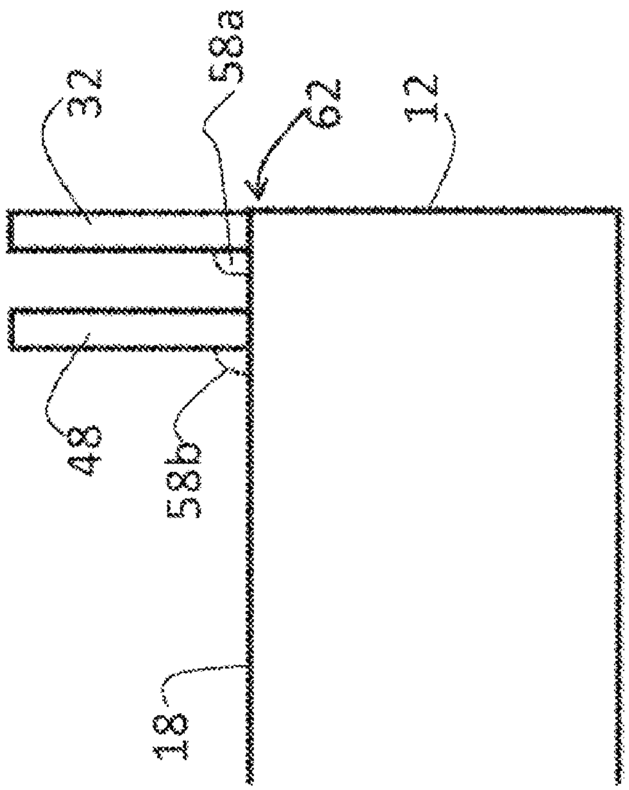

In the embodiment shown in FIG. 3D, the first and second tabs 32, 48 extend from different positions proximate to first end 12. First tab 32 extends from the intersection 62 between the first end 12 and the first parallel edge 18 of the strip 28, similar to the embodiment shown in FIG. 3C. Second tab 48, extends from slightly farther down first parallel edge 18, away from first end 18. As shown in FIG. 3D, each of first and second tab angles 58*a*, 58*b* are about 90 degrees. Although only first and second tabs 32, 48 are illustrated, it is understood that three or more tabs may be included. One of at least ordinary skill in the art will recognize that there are several configurations, regarding number of tabs, placement of tabs regarding extension from the first parallel edge, and tab angles that would successfully address the goals of the present invention. Each of these variations is considered to be within the scope of the present invention.

Figure 3E:
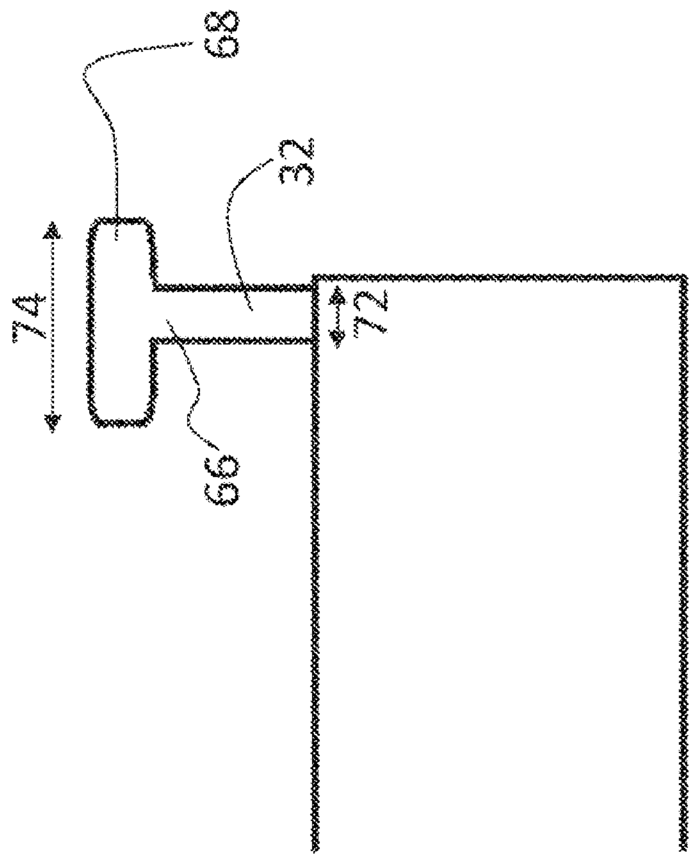
FIG. 3E is a top-down view of the first end of the strap where the tab includes an area of increased width.

In the embodiment shown in FIG. 3E, tab 32 includes an area of increased width 68 at the tab tip 66. The area of increased width 68 allows the user to hold the tab 32 in place against her palm with more than one fingertip, should she wish to do so. The area of increased width 68 is any structure disposed at the tip 66 of the tab 32 that has a greater width 74 than the tab width 72. The area of increased width 68 is shown in FIG. 3E as a simple crossbar with rounded edges. The area of increased width 68 may also be a crossbar with angled edges, a circle, oval, or any other shape with a greater width 74 than the tab width 72. The entire tab 32 may be triangle-shaped so that the point of the triangle, or the part of the triangle with the smallest width, intersects the first end 12, and the base of the triangle, or the part of the triangle with the largest width, will be grasped by the user's fingertips as the area of increased width 68. The area of increased width 68 may be cut from the same single ply of tab material 34 as the tab 32, so that the tab 32 and the area of increased width 68 are a seamless, integrated structure. Alternatively, the area of increased width 68 may be a separate piece of material that is affixed to the tab tip 66 by stitching, gluing, or other means of affixation common in the art. In embodiments where the area of increased width 68 is a separate piece of material, the area of increased width 68 is also made of a single ply of tab material 34. In other embodiments, however, the area of increased width 68 is made of another material, or tab material 34 that is reinforced.

Figure 4:
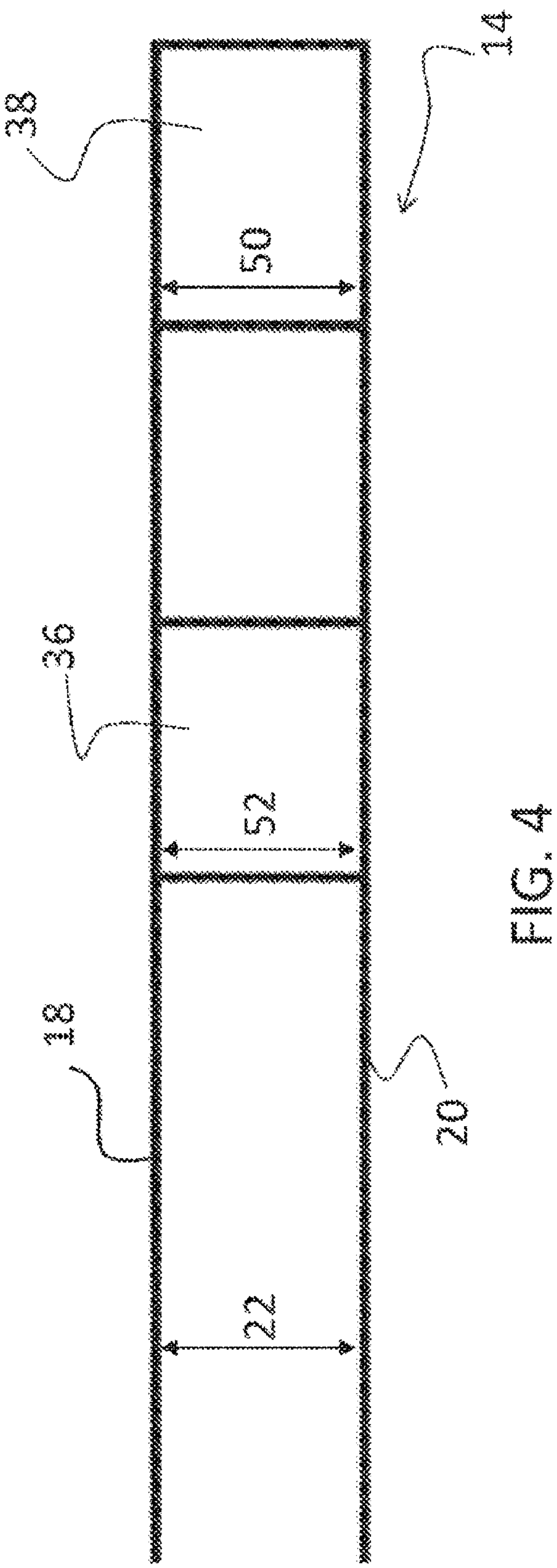
FIG. 4 is a diagram of a section of the wrist wrap according to the present invention including the second end of the strap.

Now referring to FIG. 4, alternate aspects of the first and second fastener sections 36, 38 are provided. The areas indicated as first and second fastener sections 36, 38 in FIG. 4 indicate their general position on strip 28 only, without reference to sides 24, 26 of strip 28 or the working surfaces of first and second fastener sections 36, 38. In FIGS. 1A and 1B, the first and second fastener widths 52, 50 are less than strip width 22. In embodiments such as that shown in FIG. 4, however, each of first and second fastener sections 36, 38 extends entirely between first and second parallel edges 18, 20, so that first and second fastener widths 52, 50 and strip width 22 are all equal.

Figures 5A, 5B, 5C, 5D, 5E, 5F:
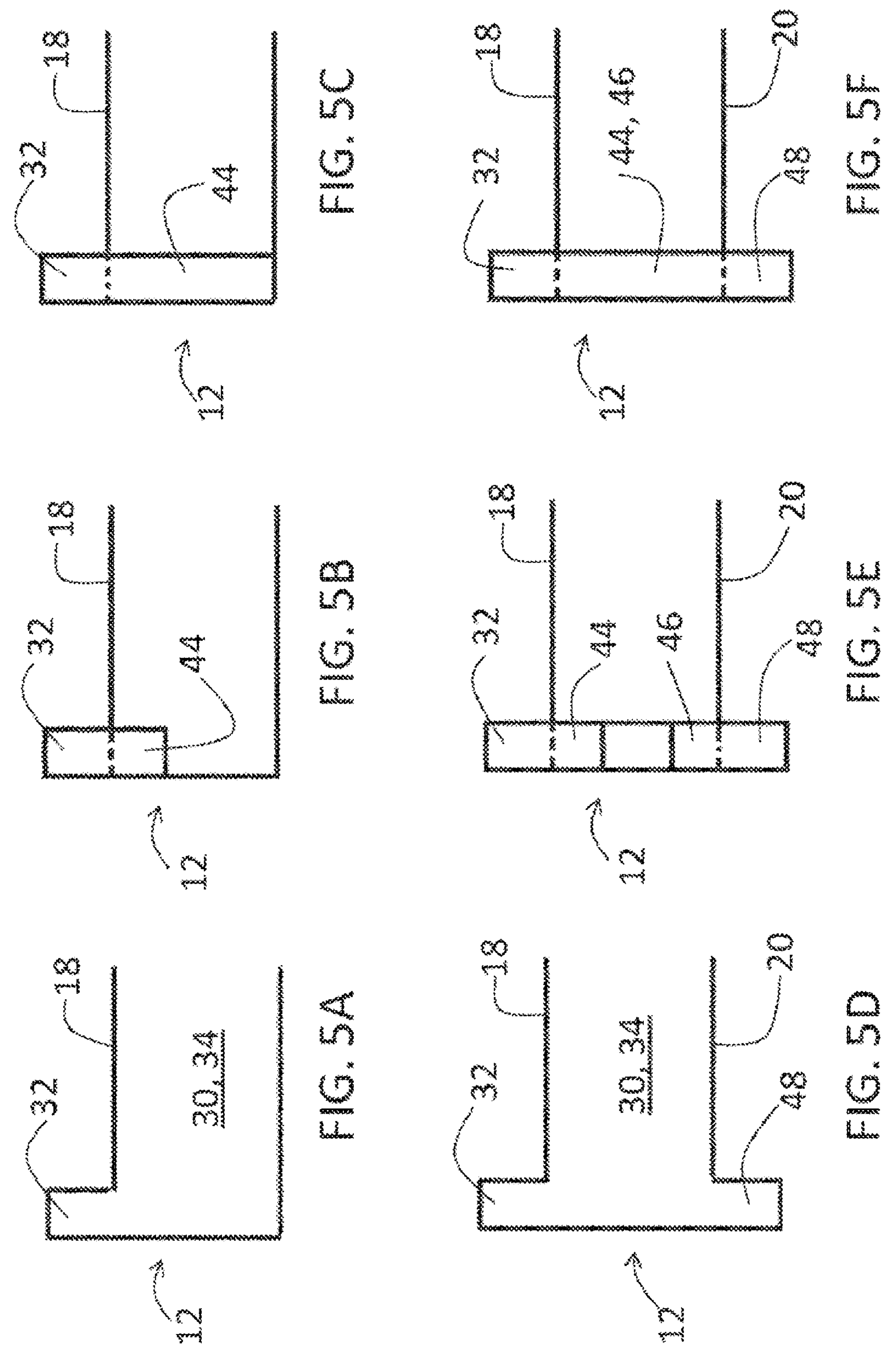
FIGS. 5A-5F are top-down diagrams of various configurations of the first end of the strap of the wrist wrap of the present invention.

Now referring to FIGS. 5A-5F, illustrations of variations on the attachment of tab 32 to strip 28 are provided. In FIG. 5A, tab material 34 and strip material 30 are the same material so that tab 32 and strip 28 are a single integrated piece. As such, tab 32 is not attached to strip 28 in this embodiment, but rather the entire wrist wrap 10 is cut from a sheet of the tab/strip material 34/30. In FIG. 5B, tab material 34 extends onto strip 22 with a first area of overlap 44. The tab 32 is affixed to the first end 12 at the first area of overlap 44 by any means commonly used in the art, such as stitching, adhering, or stitching and adhering. In FIG. 5C, the first area of overlap 44 extends across the whole first end 12 from first parallel edge 18 to second parallel edge 20. If the user wears the wrist wrap 10 with the first area of overlap 44 against her working wrist 60, then having the first area of overlap 44 extend across the width of the strip 28 may be more comfortable than the embodiment shown in FIG. 5B.

FIGS. 5D-5F illustrate embodiments of wrist wrap 10 that include first and second tabs 32, 48 extending perpendicularly from the first and second parallel edges 18, 20 of the first end 14 of the strip 28, respectively. Having the tabs 32, 48 so disposed gives the user options as to how to wrap the wrist wrap 10. All wrist wraps 10 may be worn on either hand. The wrist wrap 10 shown in FIG. 5C, for example, with only a first tab 32 may be worn on either hand, but due to the placement of the first and second fastener sections 36, 38, it must be wrapped clockwise around either the right or left hand. Pairs of wrist wraps 10 that are mirror images of one another may be sold so that one may be wrapped around one hand in one direction and the other may be wrapped around the other hand in the other direction. The wrist wrap 10 shown in FIG. 5F, for example, with first and second tabs 32, 48, may be flipped so that it may be wrapped clockwise or counterclockwise around either hand.

The embodiment shown in FIG. 5D is similar to that shown in FIG. 5A, but also includes the second tab 48. In this embodiment, like that in FIG. 5A, the tab material 34 and strip material 30 are the same and the entire wrist wrap 10 is a single integrated piece. The embodiment shown in FIG. 5E is similar to that shown in FIG. 5B, but also includes second tab 48. The tab material 34 of the second tab 48 extends onto strip 28 with a second area of overlap 46. The second tab 48 is affixed to the first end 12 at the second area of overlap 46 by any means commonly used in the art, such as stitching, adhering, or stitching and adhering.

The embodiment shown in FIG. 5F is similar to that shown in FIG. 5C, but also includes second tab 48. In FIG. 5F, the first and second areas of overlap 44, 46 extend across the whole first end 12 from first parallel edge 18 to second parallel edge 20, so that the first tab 32, first area of overlap 44, second area of overlap 46, and second tab 48 are all formed from a single piece of tab material 34.

Figure 6:
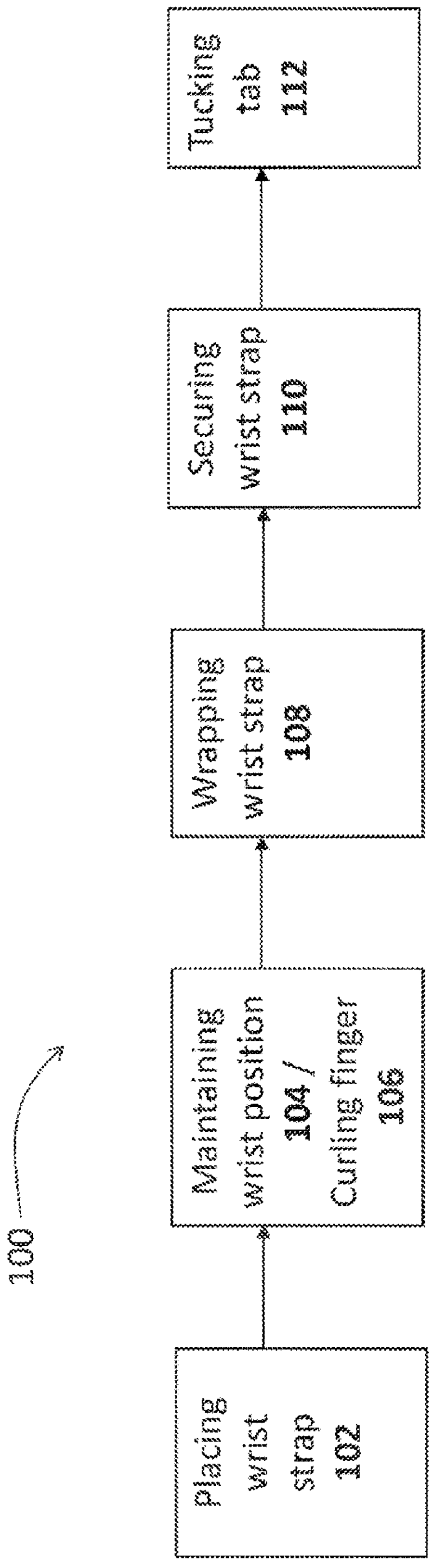
FIG. 6 is a block diagram indicating the steps of the method according to the present invention.
Figure 7:
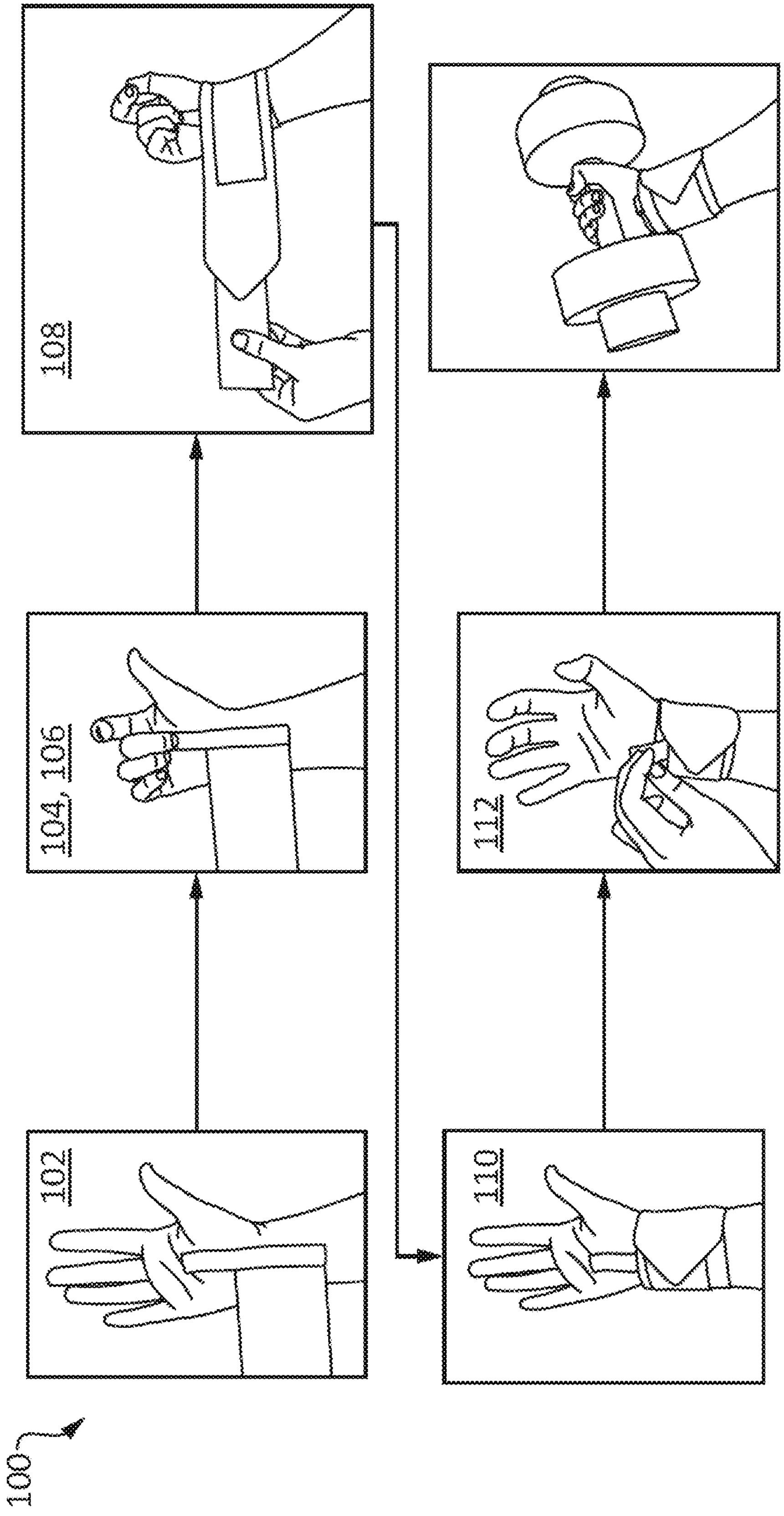
FIG. 7 is a photographic block diagram illustrating the steps of the method according to the present invention.

Now referring to FIGS. 6 and 7, written and photographic block diagrams illustrating the steps of method 100 according to the present invention for putting on the wrist strap 10 (as described above) are provided. It is understood that the working hand, working fingers, working wrist, etc. are all features of the hand and wrist onto which the wrist wrap 10 is being applied. Method 100 includes the steps of placing the wrist wrap 102 against the working wrist such that the tab extends upward over the working palm; simultaneously maintaining the working wrist 104 in a straight position while curling at least one finger 106 of the working hand down such that a tip of the finger holds a tip of the tab in place against the working palm; wrapping the strap 108 around the working wrist to a desired tension with the non-working hand; and securing the strap 110 in place by engaging the first and second fastener sections with one another. In embodiments, the method 100 also includes the step, to be performed after the securing 110 step, of tucking 112 the tab down into the wrapping of the wrist wrap.

As shown in the photographs in FIG. 7, the wrist wrap 10 is being applied to the user's right hand. In step 102, the wrist wrap 10 is placed approximately perpendicular to the arm and wrist (recognizing that the human arm, wrist, and hand do not form a perfectly straight line). The strip 28 of the wrist wrap 10 extends to the left while the tab 32 extends upward over the palm. The tab 32 is positioned at the first end 12 of the strip 28 so that none of the strip 28 is hanging out on the right where it would need to be awkwardly folded in during the wrapping 108 step. In step 104, the user is keeping her wrist perfectly straight, which is the desired position to maximize the effectiveness of the wrist wrap 10 during lifting. At the same time, she can easily perform step 106 of curling her finger down to hold the tip of tab 32 in place against her palm. Had she positioned the wrist wrap 10 farther to the left, she could have used her ring or pinky finger. Had she positioned the wrist wrap 10 farther to the right, she could have user her pointer finger. It is understood that other fingers may also be used when tab 32 is not at an approximately right angle as shown in FIG. 7, but is angled, such as with the embodiments shown in FIGS. 3A and 3B. It is also understood that more than one finger may be used when there are first and second 32, 48 or more tabs or an area of increased width 68, as in embodiments such as those shown in FIGS. 3C-3E. In the wrapping step 108, using her left hand, the user easily wraps the strip 28 around her right/working wrist. The first and second fastener sections 36, 38 are positioned so that the wrist wrap 10 is easily secured in the securing step 110. The respective areas of the first and second fastener sections 36, 38 allow the user to secure the wrist wrap at varying levels of tightness, as desired by the user for comfort and/or level of support, Finally, in the tucking step 112, the user easily tucks tab 32 into the wrapped strip 28. The tab 32 is made of a single ply of tab material 34, so it is thin and not bulky and easily slips into the wrappings without making an uncomfortable lump. Tab 32 is also typically no longer than 2 inches, so there is no unnecessary tab material 34 that needs to be forced into the tight wrappings.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

What is claimed is:

1. A wrist wrap for use in supporting a wrist during weightlifting, said wrist wrap comprising:
- a strip of strip material having:
  - a first end and a second end on opposing ends of said strip;
  - a strip length that is a distance between said first and second ends;
  - first and second parallel edges extending between said first and second ends;
  - a strip width that is a distance between said first and second parallel edges;
  - first and second opposing sides; and
  - a strip thickness that is a distance between said first and second opposing sides;
- at least one tab of tab material extending from said first end of said strip, wherein said tab is a single ply of said tab material;
- a first fastener section disposed on said first side of said strip; and
- a second fastener section disposed on said wrist wrap so as to engage said first section such that said first and sections are fastenable to one another.

2. The wrist wrap of claim 1, wherein said at least one tab forms an angle between 85 and 95 degrees with said first parallel edge.

3. The wrist wrap of claim 2, wherein:
- said at least one tab is first and second tabs;
- said first tab extends parallel from said first end such that said first tab forms an angle between 85 and 95 degrees with said first parallel edge; and
- said second tab extends parallel from said first end such that said second tab forms an angle between 85 and 95 degrees with said second parallel edge.

4. The wrist strap of claim 3, wherein:
- said tab material of said first tab extends beyond said first tab such that said tab material has a first area of overlap with said strip material and said tab material of said first tab and said strip material are affixed to one another at said first area of overlap; and
- said tab material of second first tab extends beyond said second tab such that said tab material has a second area of overlap with said strip material and said tab material of said second tab and said strip material are affixed to one another at said second area of overlap.

5. The wrist strap of claim 4, wherein said first tab, said first area of overlap, said second area of overlap, and said second tab are comprised of a single piece of tab material extending across and beyond said first end of said strip.

6. The wrist strap of claim 1, wherein said tab material extends beyond said at least one tab such that said tab material has at least one area of overlap with said strip material and said tab material and said strip material are affixed to one another at said at least one area of overlap.

7. The wrist strap of claim 6, wherein said at least one area of overlap extends entirely across said strip between said first and second parallel edges.

8. The wrist strap of claim 1, wherein said strip material and said tab material are the same, such that said strip and said at least one tab are integrated.

9. The wrist wrap of claim 1, wherein said second fastener section is disposed on said second side of said strip.

10. The wrist wrap of claim 1, wherein said second fastener section extends from said second end of said strip.

11. The wrist wrap of claim 10, wherein:
- said second fastener section comprises a second fastener width parallel to said strip width;
- said second fastener width is less than said strip width; and
- said second fastener section is centered between said first and second parallel edges of said strip.

12. The wrist wrap of claim 11, wherein:
- said second fastener section extends from said second end of said strip; and
- said second end of said strip angles inward toward said second fastener section.

13. The wrist wrap of claim 1, wherein:
- said first fastener section has a first fastener width parallel to said strip width;
- said first fastener width is less than said strip width; and
- said first fastener section is centered on said first side of said strip between said first and second parallel edges of said strip.

14. The wrist wrap of claim 1, wherein said strip material is a stretchable material.

15. The wrist wrap of claim 1, wherein said first fastener section comprises one of hook or loop fastener and said second fastener section comprises the other of hook or loop fastener.

16. The wrist wrap of claim 1, wherein said at least one tab forms an angle of between 45 and 135 degrees with said first parallel edge.

17. The wrist wrap of claim 16, wherein said at least one tab forms an angle of between 65 and 115 degrees with said first parallel edge.

18. The wrist wrap of claim 1, wherein said at least one tab is at least two tabs extending from an intersection of said first end and said first parallel edge, wherein each of said at least two tabs forms a different angle with said first parallel edge.

19. The wrist wrap of claim 1, wherein said at least one tab comprises:

a tab tip opposite from an intersection of said tab with said first end of said strip;

a tab width; and an area of increased width disposed at said tab tip, wherein said area of increased width has a width greater than said tab width.

20. A wrist wrap for use in supporting a wrist during weightlifting, said wrist wrap consisting of:

a strip of strip material having:

a first end and a second end on opposing ends of said strip;

a strip length that is a distance between said first and second ends;

first and second parallel edges extending between said first and second ends;

a strip width that is a distance between said first and second parallel edges;

first and second opposing sides; and a strip thickness that is a distance between said first and second opposing sides;

a tab of tab material extending from said first end of said strip, wherein said tab is a single ply of said tab material;

a first fastener section disposed on said first side of said strip; and a second fastener section disposed on said wrist wrap so as to engage said first section such that said first and sections are fastenable to one another.

21. The wrist wrap of claim 20, wherein said tab comprises a tab length of 1 to 2 inches.

22. The wrist wrap of claim 20, wherein tab comprises:

a tab tip opposite from an intersection of said tab with said first end of said strip;

a tab width; and an area of increased width disposed at said tab tip, wherein said area of increased width has a width greater than said tab width.

23. A method for putting a wrist wrap onto a working wrist, wherein the wrist wrap comprises a strip of strip material having a first end and a second end on opposing ends of the strip; a strip length that is a distance between the first and second ends; first and second parallel edges extending between the first and second ends; a strip width that is a distance between the first and second parallel edges; first and second opposing sides; and a strip thickness that is a distance between the first and second opposing sides; at least one tab of tab material extending from the first end of the strip, wherein the tab is a single ply of tab material; a first fastener section disposed on the first side of the strip; and a second fastener section disposed on the wrist wrap so as to engage the first section such that the first and sections are fastenable to one another, said method comprising the steps of:

placing the wrist wrap against the working wrist such that the at least one tab extends upward over the working palm;

simultaneously maintaining the working wrist in a straight position while curling at least one finger of the working hand down such that a tip of the at least one finger holds a tip of the at least one tab in place against the working palm;

wrapping the strap around the working wrist to a desired tension with the non-working hand; and securing the strap in place by engaging the first and second fastener sections with one another.

24. The method of claim 23, further comprising the step, to be performed after said securing step, of tucking the at least one tab down into the wrapping of the wrist wrap.

* * * * *